United States Patent [19]

Sakai et al.

[11] Patent Number: 5,665,711

[45] Date of Patent: Sep. 9, 1997

[54] ANTITUMOR COMPOSITION FOR ORAL ADMINISTRATION

[75] Inventors: Atsushi Sakai; Kyouichi Hirotsu; Hirotsugu Tada; Toshiyuki Shibata, all of Fukuoka, Japan

[73] Assignee: Yoshitomi Pharmaceutical Industries, Ltd., Osaka, Japan

[21] Appl. No.: 570,978

[22] Filed: Dec. 12, 1995

[51] Int. Cl.⁶ .................................................. A61K 31/70
[52] U.S. Cl. .................................................. 514/49
[58] Field of Search .................................................. 514/49

[56] References Cited

U.S. PATENT DOCUMENTS

| | | | |
|---|---|---|---|
| 5,183,882 | 2/1993 | Sakata et al. | 514/49 |
| 5,412,089 | 5/1995 | Sakata et al. | 536/28.5 |

FOREIGN PATENT DOCUMENTS 0 360 018   3/1990   European Pat. Off. .

OTHER PUBLICATIONS

Patent Abstracts of Japan, 63258818 A, Oct. 26, 1988.
Patent Abstracts of Japan, 03240731 A, Oct. 28, 1991.
Patent Abstracts of Japan, 06340531 A, Dec. 13, 1994.

*Primary Examiner*—Jerome D. Goldberg
*Attorney, Agent, or Firm*—Wenderoth, Lind & Ponack

[57] ABSTRACT

An antitumor composition for oral administration, comprising a 2'-deoxy-2'-methylidenecytidine compound of the formula

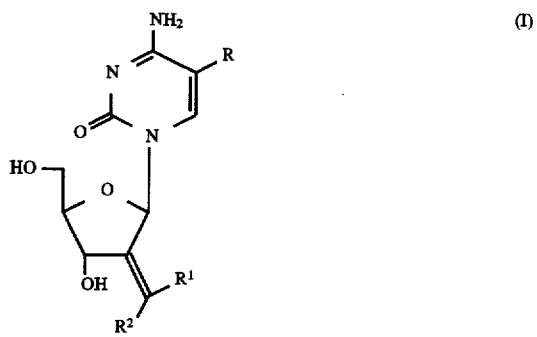

wherein R is a hydrogen or a halogen, and $R^1$ and $R^2$ are the same or different and each is a hydrogen, a halogen or an alkyl having 1 to 4 carbon atoms, an acid addition salt thereof or a hydrate thereof, and a sucrose ester of fatty acid(s). The pharmaceutical composition of the present invention comprising a DMDC compound useful as an antitumor agent based on its remarkable degenerative action on solid tumor shows an improved oral absorption.

5 Claims, No Drawings

ANTITUMOR COMPOSITION FOR ORAL ADMINISTRATION

FIELD OF THE INVENTION

The present invention relates to a pharmaceutical composition improved in oral absorption, comprising a 2'-deoxy-2'-methylidenecytidine compound useful as an antitumor agent by its remarkable degenerative effect on solid tumor, an acid addition salt thereof or a hydrate thereof. The composition can be used in the medical field.

BACKGROUND OF THE INVENTION

It has been known that 2'-deoxy-2'-methylidenecytidine (hereinafter sometimes abbreviated as DMDC), acid addition salts thereof and hydrates thereof are useful as antitumor agents (Japanese Patent Unexamined Publication Nos. 258818/1988, 138292/1990 and 240794/1991).

A DMDC dihydrate has been confirmed to exhibit superior antitumor effects and is in use in clinical situations as an injection (Japanese Patent Unexamined Publication No. 240731/1991). An administration route by injection not only burdens patients with pain but is associated with difficulties in terms of topical injuries at the injection site and the need for regular visit to the hospital for medical treatments. Hence, the development of an oral agent which resolves these problems has been desired.

For this end, the present inventors have done a multitude of basic experiments and found that an increase in dose results in a marked decrease in oral absorption, as a result of which bioavailability of DMDC dihydrate becomes low. To be specific, a radioactively labeled DMDC dihydrate was orally administered to rats, and urinary excretion thereof (% relative to dose) within 24 hours was examined to determine the oral absorption of DMDC dihydrate. As a result, the percent excretion was 74.4±1.4% at the dose of 3 mg/kg and decreased to 47.2±9.6% at the dose of 30 mg/kg. For sufficient pharmacological action to be exerted by oral administration, an appropriate treatment should desirably be applied during preparation to promote the oral absorption of DMDC dihydrate.

As the absorption promoter used for improving oral absorption, there have been known fatty acids having 8 to 14 carbon atoms such as sodium caprate. Then, a composition containing sodium caprate and DMDC dihydrate was studied only to find no improvement in the oral absorption.

Also, surfactants are used for liquid agents and semi-liquid agents for improving wettability of the drug to water. It is not generally practiced, however, to add a surfactant to DMDC dihydrate of the present invention which is a solid preparation and has high wettability to water. Moreover, addition of non-ionic surfactant such as polyoxyethylene hydrogenated castor oil and polyoxyethylene (20) sorbitan monoleate did not lead to an improvement in oral absorption.

In contrast, when sodium oleate or sodium lauryl sulfate was added, absorption in situ improved, whereas urinary excretion in vivo was problematically poor. Accordingly, preparations containing these compounds pose problems in terms of stability and mucosal disorders.

It is therefore an object of the present invention to provide an antitumor composition improved in oral absorption, comprising a 2'-deoxy-2'-methylidenecytidine compound represented by DMDC dihydrate.

SUMMARY OF THE INVENTION

According to the present invention, it has now been found that a sucrose ester of fatty acid(s), particularly, that having an HLB value [Hydrophilic-lipophilic balance: Journal of the Society of Cosmetic Chemists, 1311–1326 (1949)] of about 10–20 exhibits extremely superior effects in improving the oral absorption of DMDC dihydrate at high doses.

The present invention provides the following.

(1) An antitumor composition for oral administration, which comprises a 2'-deoxy-2'-methylidenecytidine compound of the formula

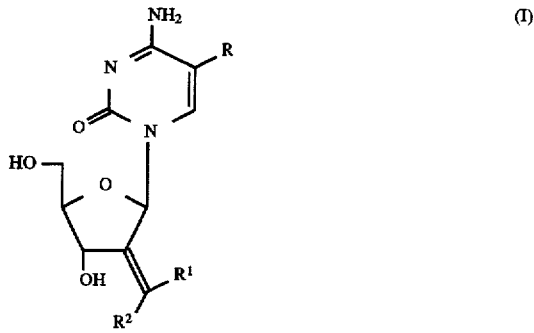

wherein R is a hydrogen or a halogen, and $R^1$ and $R^2$ are the same or different and each is a hydrogen, a halogen or an alkyl having 1 to 4 carbon atoms, an acid addition salt thereof or a hydrate thereof, and a sucrose ester of fatty acid(s).

(2) The antitumor composition for oral administration of the above (1), wherein the sucrose ester of fatty acid(s) has an HLB value of about 10–20.

(3) The antitumor composition for oral administration of the above (1), wherein the sucrose ester of fatty acid(s) is contained in a 0.1–20-fold amount by weight relative to the compound of the formula (I), an acid addition salt thereof or a hydrate thereof.

(4) The antitumor composition for oral administration of the above (1), wherein the 2'-deoxy-2'-methylidenecytidine compound of the formula (I), an acid addition salt thereof or a hydrate thereof is selected from the group consisting of 2'-deoxy-2'-methylidenecytidine dihydrate, 2'-deoxy-2'-methylidenecytidine hydrochloride ½ hydrate, 2'-deoxy-2'-methylidene-5-fluorocytidine, 2'-deoxy-2'-fluoromethylidenecytidine and 2'-deoxy-2'-ethylidenecytidine.

(5) The antitumor composition for oral administration of the above (1), wherein the 2'-deoxy-2'-methylidenecytidine compound of the formula (I), an acid addition salt thereof or a hydrate thereof is a 2'-deoxy-2'-methylidenecytidine dihydrate.

DETAILED DESCRIPTION OF THE INVENTION

In the formula (I), halogen means chlorine, bromine, fluorine or iodine, and alkyl having 1 to 4 carbon atoms means, for example, methyl, ethyl, propyl, isopropyl, butyl, isobutyl and tert-butyl. The acid addition salt is exemplified by inorganic acid salts such as hydrochloride, hydrobromide, sulfate and phosphate, and organic acid salts such as maleate, fumarate, tartrate, succinate, citrate, benzenesulfonate and pamoate; and hydrate includes, for example, ½ hydrate, monohydrate, ½ hydrate and dihydrate.

Examples of 2'-deoxy-2'-methylidenecytidine compound of the formula (I), acid addition salt thereof and hydrate thereof include 2'-deoxy-2'-methylidenecytidine dihydrate (DMDC dihydrate), 2'-deoxy-2'-methylidenecytidine hydrochloride ½ hydrate, 2'-deoxy-2'-methylidene-5-fluorocytidine (5F-DMDC), 2'-deoxy-2'-fluoromethylidenecytidine (FMdC) and 2'-deoxy-2'-ethylidenecytidine.

The sucrose ester of fatty acid(s) to be used as an absorption promoter is generally called sugar ester and is a safe substance widely used as a food additive. The sucrose ester of fatty acid(s) to be used in the present invention is preferably that wherein fatty acid has 8 to 25 carbon atoms, and may be naturally occurring or synthetic, with preference given to naturally occurring ones. Such fatty acid may be linear or branched, preferably linear. Examples of preferable fatty acid include caproic acid, capric acid, myristic acid, stearic acid, palmitic acid, lauric acid and oleic acid. Sucrose has three primary alcohol hydroxys, and sucrose ester of fatty acid(s) includes those bonded with one fatty acid (monoester type), two fatty acids (diester type) or three fatty acids (triester type). It may be a mixture of monoester, diester and triester, or a mixed ester of 2 or 3 kinds of the above-mentioned fatty acids.

In the present invention, a higher mixing ratio of monoester type sucrose ester of fatty acid(s) means more superior oral absorption. The present invention has clarified that a sucrose ester of fatty acid(s) having a higher HLB value, in particular, that having an HLB value of about 10–20 shows superior promotion of oral absorption. Specifically speaking, Ryoto sugar esters S-1170, S-1570, S-1670, P-1570, P-1670 and OWA-1570 manufactured by Mitsubishi Kasei Shokuhin and DK esters F-110, F-140, F-160 and SS manufactured by DAI-ICHI KOGYO SEIYAKU CO., LTD. are exemplified.

Alternatively, the above-mentioned sucrose ester of fatty acid(s) and two or more kinds of sucrose esters of fatty acid(s) having HLB values other than about 10–20, such as Ryoto sugar esters S-970 and LWA-1570 are mixed to adjust the HLB value to about 10–20 before The sucrose ester of fatty acid(s) can be used in a 0.1–20-fold amount by weight relative to the 2'-deoxy-2'-methylidenecytidine compound of the formula (I), with preference given to, but not limited to, 0.5–10-fold amount by weight, wherein the amount can be appropriately determined. The composition of the present invention contains about 5–500 mg of the compound of the formula (I) in one preparation.

The antitumor composition for oral administration of the present invention is formulated into, for example, liquid preparations such as syrup and suspension, or solid preparations such as granules, fine granules, capsule and tablet, with preference given to solid preparations.

The above-mentioned preparations can be produced by a conventional method. For example, syrup and suspension can be obtained by dissolving or suspending the compound of the formula (I) and a sucrose ester of fatty acid(s) in water or a suitable aqueous solution such as hydroxypropylmethylcellulose solution and carboxymethylcellulose solution. Granules and fine granules can be obtained by mixing the compound of the formula (I) and a sucrose ester of fatty acid(s) in a powdery state, adding, as necessary, excipient such as sucrose and lactose and binder such as hydroxypropylmethylcellulose, kneading, granulating by an extrusion granulator equipped with a screen having a diameter of 0.5–1 mm, drying, and classifying by passing the granules through sieves. Capsule can be obtained by filling capsules with powder, granules or fine granules obtained above. Tablet can be obtained by adding conventionally-employed additives such as excipients (e.g. lactose, corn starch and microcrystalline cellulose), binders (e.g. hydroxypropylcellulose, hydroxypropylmethylcellulose and polyvinylpyrrolidone) and disintegrators (e.g. low substituted hydroxypropylcellulose and calcium carboxymethylcellulose) to a mixture of the compound of the formula (I) and a sucrose ester of fatty acid(s), kneading and granulating by wet granulation method or dry granulation method, adding lubricants such as light anhydrous silicic acid and magnesium stearate to granules, and compressing. The tablets can be prepared into sugar-coated tablets or film-coated tablets by a conventional method.

The composition of the present invention has achieved a remarkable improvement in the absorption from digestive tracts by the addition of a sucrose ester of fatty acid(s) to the compound of the formula (I) which is useful as an antitumor agent. The composition having an improved oral absorption at high dose of the compound of the formula (I) can accomplish high bioavailability and superior characteristics as an antitumor agent for internal use. In addition, sucrose ester of fatty acid(s) is a safe substance widely used as a food additive, and desirable from practical aspects.

The composition of the present invention enables oral administration of the compound of the formula (I) such as DMDC dihydrate, and can be easily used for the treatment or prophylaxis, or home therapy, and maintenance therapy after treatment of solid tumor and the like. The active ingredient is administered in the dose of about 50–500 mg daily to an adult, though the amount is subject to suitable increases.

The present invention is described in detail by illustrative Examples, to which the present invention is not limited.

EXAMPLE 1

A 0.5% aqueous hydroxypropylmethylcellulose solution (0.8 ml) is added to dissolve 2'-deoxy-2'-methylidenecytidine dihydrate (6.9 mg) and a sucrose ester of fatty acid(s) (4.0 mg) having an HLB value of 19 wherein conjugated fatty acid comprises about 70% stearic acid and about 30% palmitic acid, ester composition being about 100% monoester, whereby an aqueous solution is prepared.

EXAMPLE 2

A 0.5% aqueous hydroxypropylmethylcellulose solution (5 ml) is added to dissolve 2'-deoxy-2'-methylidenecytidine dihydrate (30 mg) and a sucrose ester of fatty acid(s) (90 mg) having an HLB value of 15 wherein conjugated fatty acid comprises about 70% stearic acid and about 30% palmitic acid, ester composition being about 75% monoester and about 25% ditriester, whereby an aqueous solution is prepared.

EXAMPLE 3

A 0.5% aqueous hydroxypropylmethylcellulose solution (5 ml) is added to dissolve 2'-deoxy-2'-methylidenecytidine dihydrate (30 mg) and a sucrose ester of fatty acid(s) (90 mg) having an HLB value of 11 wherein conjugated fatty acid comprises about 70% stearic acid and about 30% palmitic acid, ester composition being about 50% monoester and about 50% ditriester, whereby an aqueous solution is prepared.

EXAMPLE 4

A 0.5% aqueous hydroxypropylmethylcellulose solution (5 ml) is added to dissolve 2'-deoxy-2'-methylidenecytidine dihydrate (30 mg) and a sucrose ester of fatty acid(s) (90 mg) having an HLB value of 16 wherein conjugated fatty acid comprises about 20% stearic acid and about 80% palmitic acid, ester composition being about 80% monoester and about 20% ditriester, whereby an aqueous solution is prepared.

EXAMPLE 5

A 0.5% aqueous hydroxypropylmethylcellulose solution (5 ml) is added to dissolve 2'-deoxy-2'-methylidenecytidine dihydrate (30 mg) and a sucrose ester of fatty acid(s) (90 mg) having an HLB value of 16 wherein conjugated fatty acid comprises about 70% stearic acid and about 30% palmitic acid, ester composition being about 75% monoester and about 25% ditriester, whereby an aqueous solution is prepared.

EXAMPLE 6

A 0.5% aqueous hydroxypropylmethylcellulose solution (5 ml) is added to dissolve 2'-deoxy-2'-methylidenecytidine dihydrate (30 mg) and a sucrose ester of fatty acid(s) (30 mg) having an HLB value of 19 wherein conjugated fatty acid comprises about 70% stearic acid and about 30% palmitic acid, ester composition being about 100% monoester, whereby an aqueous solution is prepared.

EXAMPLE 7

A 0.5% aqueous hydroxypropylmethylcellulose solution (5 ml) is added to dissolve 2'-deoxy-2'-methylidenecytidine dihydrate (30 mg) and a sucrose ester of fatty acid(s) (90 mg) having an HLB value of 19 wherein conjugated fatty acid comprises about 70% stearic acid and about 30% palmitic acid, ester composition being about 100% monoester, whereby an aqueous solution is prepared.

EXAMPLE 8

A 0.5% aqueous hydroxypropylmethylcellulose solution (5 ml) is added to dissolve 2'-deoxy-2'-methylidenecytidine dihydrate (30 mg) and a sucrose ester of fatty acid(s) (150 mg) having an HLB value of 19 wherein conjugated fatty acid comprises about 70% stearic acid and about 30% palmitic acid, ester composition being about 100% monoester, whereby an aqueous solution is prepared.

EXAMPLE 9

A 0.5% aqueous hydroxypropylmethylcellulose solution (5 ml) is added to dissolve 2'-deoxy-2'-methylidenecytidine dihydrate (30 mg) and a sucrose ester of fatty acid(s) (300 mg) having an HLB value of 19 wherein conjugated fatty acid comprises about 70% stearic acid and about 30% palmitic acid, ester composition being about 100% monoester, whereby an aqueous solution is prepared.

EXAMPLE 10

2'-Deoxy-2'-methylidenecytidine dihydrate (1 part by weight), a sucrose ester of fatty acid(s) (1 part by weight) having an HLB value of 19 wherein conjugated fatty acid comprises about 70% stearic acid and about 30% palmitic acid, ester composition being about 100% monoester, sucrose (2 parts by weight) and hydroxypropylmethylcellulose (0.2 part by weight) as a binder are kneaded, granulated by an extrusion granulator equipped with a screen having a diameter of 1 mm, dried at a temperature of not more than 30° C., and classified by passing the granules through sieves to give a granular agent.

EXAMPLE 11

2'-Deoxy-2'-methylidenecytidine dihydrate (1 part by weight), a sucrose estser of fatty acid(s) (3 parts by weight) having an HLB value of 16 wherein conjugated fatty acid comprises about 70% stearic acid and about 30% palmitic acid, ester composition being about 75% monoester and about 25% ditriester, low substituted hydroxypropylcellulose (2 parts by weight) and hydroxypropylmethylcellulose (0.2 part by weight) as a binder are kneaded and granulated, and the obtained granules are filled in capsules.

EXAMPLE 12

2'-Deoxy-2'-methylidenecytidine dihydrate (1 part by weight), a sucrose ester of fatty acid(s) (2 parts by weight) having an HLB value of 11 wherein conjugated fatty acid comprises about 70% stearic acid and about 30% palmitic acid, ester composition being about 50% monoester and about 50% ditriester, lactose (8 parts by weight) and hydroxypropylmethylcellulose (0.2 part by weight) as a binder are kneaded, granulated by an extrusion granulator equipped with a screen having a diameter of 0.5 mm, dried at a temperature of not more than 30° C., and classified by passing the granules through sieves to give a fine granular agent.

EXAMPLE 13

2'-Deoxy-2'-methylidenecytidine dihydrate (1 part by weight), a sucrose ester of fatty acid(s) (5 parts by weight) having an HLB value of 16 wherein conjugated fatty acid comprises about 70% stearic acid and about 30% palmitic acid, ester composition being about 80% monoester and about 20% ditriester, low substituted hydroxypropylcellulose (2 parts by weight) and polyvinylpyrrolidone (0.2 part by weight) as a binder are kneaded and granulated, and the obtained granules are filled in capsules.

EXAMPLE 14

2'-Deoxy-2'-methylidenecytidine dihydrate (1 part by weight), a sucrose ester of fatty acid(s) (1 part by weight) having an HLB value of 19 wherein conjugated fatty acid comprises about 70% stearic acid and about 30% palmitic acid, ester composition being about 100% monoester, lactose (0.2 part by weight), microcrystalline cellulose (0.8 part by weight) and hydroxypropylmethylcellulose (0.2 part by weight) as a binder are kneaded, pulverized, dried and passed through a 24 mesh sieve to give granules. Magnesium stearate is added and mixed, and the mixture is compressed to give tablets.

EXAMPLE 15

2'-Deoxy-2'-methylidenecytidine dihydrate (1 part by weight), a sucrose ester of fatty acid(s) (0.5 part by weight) having an HLB value of 16 wherein conjugated fatty acid comprises about 70% stearic acid and about 30% palmitic acid, ester composition being about 75% monoester and about 25% ditriester, sugar powder (1 part by weight) and hydroxypropylcellulose (0.2 part by weight) as a binder are kneaded, pulverized, dried and passed through a 24 mesh sieve to give granules. Calcium carboxymethylcellulose (1 part by weight) and magnesium stearate are added and mixed, and the mixture is compressed to give tablets.

EXAMPLE 16

2'-Deoxy-2'-methylidenecytidine dihydrate (1 part by weight), a sucrose ester of fatty acid(s) (2 parts by weight)

having an value of 11 wherein conjugated fatty acid comprises about 70% stearic acid and about 30% palmitic acid, ester composition being about 50% monoester and about 50% ditriester, low substituted hydroxypropylcellulose (2 parts by weight) and hydroxypropylmethylcellulose (0.2 part by weight) as a binder are kneaded, pulverized, dried and passed through a 24 mesh sieve to give granules. Magnesium stearate is added and mixed, and the mixture is compressed to give tablets.

EXAMPLE 17

2'-Deoxy-2'-methylidenecytidine dihydrate (1 part by weight), a sucrose ester of fatty acid(s) (3 parts by weight) having an HLB value of 16 wherein conjugated fatty acid comprises about 70% stearic acid and about 30% palmitic acid, ester composition being about 80% monoester and about 20% ditriester, low substituted hydroxypropylcellulose (6 parts by weight) and magnesium stearate are mixed, compressed by a conventional method, pulverized and passed through a sieve. The granules thus prepared are again compressed to give tablets.

EXAMPLE 18

2'-Deoxy-2'-methylidenecytidine dihydrate (1 part by weight), a sucrose ester of fatty acid(s) (1 part by weight) having an HLB value of 19 wherein conjugated fatty acid comprises about 70% stearic acid and about 30% palmitic acid, ester composition being about 100% monoester, lactose (8 parts by weight) and low substituted hydroxypropylcellulose (0.2 part by weight) as a binder are prepared into granules by wet granulation. The obtained granules are placed in a coating pan and subjected to spray coating by a conventional method using an alcohol solution of methacrylic acid copolymer L (Eudragit L®) to give granules in a 10% increased weight, whereby an enteric-coated preparation is obtained.

By the similar procedures as in Examples 1 to 18, compositions containing 2'-deoxy-2'-methylidenecytidine hydrochloride ½ hydrate, 2'-deoxy-2'-methylidene-5-fluorocytidine, 2'-deoxy-2'-fluoromethylidenecytidine or 2'-deoxy-2'-ethylidenecytidine can be prepared.

The results of representative experiments with regard to the above Examples (compositions of the present invention) are given in the following to show the action and effects of the present invention. The compositions prepared in the following Preparative Examples were used for comparison.

Preparative Example 1

2'-Deoxy-2'-methylidenecytidine dihydrate (6.9 mg) is dissolved in a 0.5% aqueous hydroxypropylmethylcellulose solution (0.8 ml) to give an aqueous solution.

Preparative Example 2

2'-Deoxy-2'-methylidenecytidine dihydrate (6.9 mg) and sodium caprate (6.9 mg) are dissolved in a 0.5% aqueous hydroxypropylmethylcellulose solution (0.8 ml) to give an aqueous solution.

Preparative Example 3

2'-Deoxy-2'-methylidenecytidine dihydrate (6.9 mg) and polyoxyethylene (20) sorbitan monooleate (4.0 mg) are dissolved in a 0.5% aqueous hydroxypropylmethylcellulose solution (0.8 ml) to give an aqueous solution.

Preparative Example 4

2'-Deoxy-2'-methylidenecytidine dihydrate (6.9 mg) and polyoxyethylene hydrogenated castor oil (4.0 mg) are dissolved in a 0.5% aqueous hydroxypropylmethylcellulose solution (0.8 ml) to give an aqueous solution.

Preparative Example 5

2'-Deoxy-2'-methylidenecytidine dihydrate (30 mg) is dissolved in a 0.5% aqueous hydroxypropylmethylcellulose solution (5 ml) to give an aqueous solution.

Preparative Example 6

2'-Deoxy-2'-methylidenecytidine dihydrate (6.9 mg) and sodium oleate (6.9 mg) are dissolved in a 0.5% aqueous hydroxypropylmethylcellulose solution (0.8 ml) to give an aqueous solution.

Preparative Example 7

2'-Deoxy-2'-methylidenecytidine dihydrate (6.9 mg) and sodium lauryl sulfate (4.0 mg) are dissolved in a 0.5% aqueous hydroxypropylmethylcellulose solution (0.8 ml) to give an aqueous solution.

Test 1: in situ loop test

The aqueous solutions obtained in Example 1 and Preparative Examples 1–4, 6 and 7 were used as test samples. The test animals were 7–8 weeks old male Sprague-Dawley rats weighing 200–250 g and fasted overnight, and were used by 4 per group. Each rat underwent 10 cm long loop 1 formation and 10 cm long loop formation at duodenum under light etherization. DMDC dihydrate alone (Preparative Example 1) was administered into loop 1 and DMDC dihydrate plus absorption promoter (Example 1, Preparative Examples 2–4, 6 and 7) into loop 2 of two rats out of four of one group; and DMDC dihydrate plus absorption promoter (Example 1, Preparative Examples 2–4, 6 and 7) into loop 1 and DMDC dihydrate alone (Preparative Example 1) into loop 2 of the remaining two rats. At 2 hours from the administration, the residual amount in each loop was determined, and the absorption ratio was calculated from the difference between the amount administered into the loop and the residual amount in the loop.

The results are shown in Table 1, wherein the absorption ratio is mean±standard deviation.

TABLE 1

| Sample | Absorption promoter | Composition ratio* | Absorption (%) |
|---|---|---|---|
| Ex. 1 Prep. Ex. | sucrose ester of fatty acid(s) | x0.6 | 80.6 ± 8.1 |
| 1 | without addition | 0 | 18.1 ± 5.4 |
| 2 | sodium caprate | x1.0 | 21.4 ± 4.8 |
| 3 | polyoxyethylene (20) sorbitan oleate | x0.6 | 19.1 ± 4.7 |
| 4 | polyoxyethylene hydrogenated castor oil | x0.6 | 14.3 ± 4.0 |
| 6 | sodium oleate | x1.0 | 34.7 ± 7.1 |
| 7 | sodium lauryl sulfate | x0.6 | 60.3 ± 15.8 |

Note:
*is a composition ratio by weight of absorption promoter relative to DMDC dihydrate.

The above test results show a markedly improved absorption ratio of DMDC dihydrate in the oral preparation (Example 1) of the present invention added with a sucrose ester of fatty acid(s) as compared to the preparation (Preparative Example 1) without an absorption promoter. The preparations (Preparative Examples 2–4) added with a conventional absorption promoter failed to improve the absorption of DMDC dihydrate.

On the other hand, while the preparation added with sodium oleate or particularly sodium lauryl sulfate showed remarkable improvement in the absorption, the preparations added with these compounds showed problematic inferiority in urinary excretion as shown in the following Experimental Example 2.

Test 2: Absorption and excretion test

As the test animals, used were 7–8 weeks old male Sprague-Dawley rats weighing 200–250 g and fasted overnight, which were used by 4 per group. Each rat was orally administered, as a test preparation, with the preparation of the present invention obtained in Examples 2 to 9 and the preparation obtained in Preparative Example 5 as a control preparation. Rat urine up to 24 hours after the administration was collected and the concentration of DMDC dihydrate in the urine was measured by high performance liquid chromatography.

Urinary excretion of DMDC dihydrate was calculated by the following formula.

$$\text{Urinary excretion (\%)} = \frac{\text{Urinary concentration (mg/ml)} \times \text{urine amount (ml)}}{\text{Administered amount (mg)}} \times 100$$

The results are shown in Table 2. Urinary excretion ratio is mean±standard deviation.

TABLE 2

| | Sucrose ester of fatty acid(s) | | | Urinary excretion |
|---|---|---|---|---|
| | type | HLB value | Composition ratio* | %, 0–24 hr |
| Ex. 2 | F-160[1] | 15 | ×3 | 73.7 ± 3.0 |
| Ex. 3 | F-110[1] | 11 | ×3 | 64.8 ± 5.9 |
| Ex. 4 | P-1670[2] | 16 | ×3 | 78.3 ± 6.9 |
| Ex. 5 | S-1670[2] | 16 | ×3 | 78.4 ± 1.5 |
| Ex. 6 | SS[1] | 19 | ×1 | 56.0 ± 12.4 |
| Ex. 7 | SS[1] | 19 | ×3 | 78.1 ± 5.5 |
| Ex. 8 | SS[1] | 19 | ×5 | 82.7 ± 8.0 |
| Ex. 9 | SS[1] | 19 | ×10 | 85.2 ± 5.1 |
| Prep. Ex. 5 | — | — | — | 47.2 ± 9.6 |

Note:
*is a composition ratio by weight of absorption promoter relative to DMDC dihydrate.
[1]DK ester manufactured by DAI-ICHI KOGYO SEIYAKU CO., LTD.
[2]Ryoto sugar ester manufactured by Mitsubishi Kasei Shokuhin The above test results show a markedly improved urinary excretion ratio of DMDC dihydrate in the oral preparations (Examples 2–9) of the present invention added with an absorption promoter (sucrose ester of fatty acid(s)) as compared to the preparation (Preparative Example 5) without an absorption promoter.

The use of sodium oleate (composition ratio:×1) or sodium lauryl sulfate (composition ratio:×0.2) instead of sucrose ester of fatty acid(s) in the similar absorption excretion test did not show remarkable improvement.

sodium oleate: 51.6±6.3 (%)

sodium lauryl sulfate: 46.4±7.6 (%)

The results of various tests inclusive of these Experimental Examples reveal improved absorption ratio of DMDC dihydrate from the digestive tracts, particularly in high dose preparations, as well as greatly improved urinary excretion ratio, which was achieved by the addition of sucrose ester of fatty acid(s). Accordingly, the composition of the present invention is useful as a DMDC dihydrate preparation improved in oral absorption.

What is claimed is:

1. An antitumor composition for oral administration, comprising an effective amount of a 2'-deoxy-2'-methylidenecytidine compound of the formula

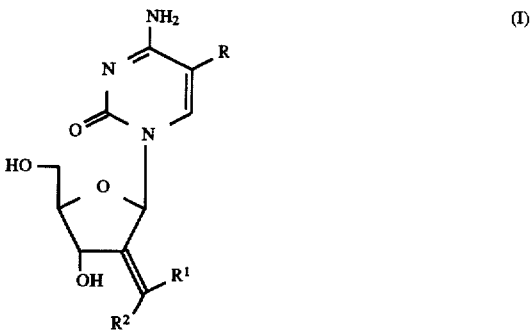

wherein R is a hydrogen or a halogen, and $R^1$ and $R^2$ are the same or different and each is a hydrogen, a halogen or an alkyl having 1 to 4 carbon atoms, an acid addition salt thereof or a hydrate thereof, and a sucrose ester of fatty acid(s), wherein said tumor is sensitive to treatment with said compound.

2. The antitumor composition for oral administration of claim 1, wherein the sucrose ester of fatty acid(s) has an HLB value of about 10–20.

3. The antitumor composition for oral administration of claim 1, wherein the sucrose ester of fatty acid(s) is comprised in a 0.1–20-fold amount by weight relative to the compound of the formula (I), an acid addition salt thereof or a hydrate thereof.

4. The antitumor composition for oral administration of claim 1, wherein the 2'-deoxy-2'-methylidenecytidine compound of the formula (I), an acid addition salt thereof or a hydrate thereof is selected from the group consisting of 2'-deoxy-2'-methylidenecytidine dihydrate, 2'-deoxy-2'-methylidenecytidine hydrochloride ½ hydrate, 2'-deoxy-2'-methylidene-5-fluorocytidine, 2'-deoxy-2'-fluoromethylidenecytidine and 2'-deoxy-2'-ethylidenecytidine.

5. The antitumor composition for oral administration of claim 1, wherein the 2'-deoxy-2'-methylidenecytidine compound of the formula (I), an acid addition salt thereof or a hydrate thereof is a 2'-deoxy-2'-methylidenecytidine dihydrate.

* * * * *